(12) United States Patent
Campbell et al.

(10) Patent No.: US 6,626,823 B1
(45) Date of Patent: Sep. 30, 2003

(54) IMPLANT MATERIAL

(75) Inventors: Julie Hazel Campbell, Brookfield (AU); Gordon Ronald Campbell, Brookfield (AU)

(73) Assignee: The University of Queeland of St. Lucia (AU)

( * ) Notice: Subject to any disclaimer, the term of this patent is extended or adjusted under 35 U.S.C. 154(b) by 0 days.

(21) Appl. No.: 09/763,359
(22) PCT Filed: Aug. 20, 1999
(86) PCT No.: PCT/AU99/00670

§ 371 (c)(1),
(2), (4) Date: May 15, 2001

(87) PCT Pub. No.: WO00/10620
PCT Pub. Date: Mar. 2, 2000

(30) Foreign Application Priority Data

Aug. 21, 1998 (AU) .............................................. PP5422
Dec. 22, 1998 (AU) .............................................. PP7859

(51) Int. Cl.[7] ................................................. A61F 2/04
(52) U.S. Cl. .......................................... 600/36; 623/916
(58) Field of Search ............................... 623/1.1, 1.41, 623/1.44, 11.11, 12, 901, 915, 916, 921, 924, 925; 606/151, 153, 191, 192, 194, 195, 198; 600/36; 604/7, 8

(56) References Cited

U.S. PATENT DOCUMENTS

| | | | | |
|---|---|---|---|---|
| 3,625,198 A | * | 12/1971 | Sparks | 264/137 |
| 4,490,137 A | * | 12/1984 | Moukheibir | 604/116 |
| 6,110,188 A | * | 8/2000 | Narciso, Jr. | 606/153 |
| 6,117,166 A | * | 9/2000 | Winston et al. | 623/1.13 |

FOREIGN PATENT DOCUMENTS

| | | |
|---|---|---|
| EP | 393 788 A | 10/1990 |
| EP | 0 393 788 A2 | 10/1990 |
| EP | 0 470 681 A2 | 2/1992 |
| EP | 470 681 A | 2/1992 |
| EP | 0 597 810 A2 | 5/1994 |
| EP | 597 810 A | 5/1994 |

OTHER PUBLICATIONS

Campbell et al. "Cytodifferentiation and Expression of α–Smooth Muscle Actin mRNA and Protein during Primary Culture of Aortic Smooth Muscle Cells" *Arteriosclerosis* 9(5): 633–643, 1989.

Desmouliere et al. "Role of the myofibroblast differentiation during liver fibrosis" *Journal of Hepatology* 22:61–64, 1995.

Edwards et al. "Development of an Ovine Collagen–based Composite Biosynthetic Vascular Prosthesis" *Clinical Material* 9:211–223, 1992.

(List continued on next page.)

*Primary Examiner*—David J. Isabella
*Assistant Examiner*—Urmi Chattopadhyay
(74) *Attorney, Agent, or Firm*—Morrison & Foerster, LLP

(57) ABSTRACT

Disclosed are tissue implant materials for use in grafting procedures. More particularly non-vascular tissue for use as vascular graft material and a method of vascular grafting using non-vascular tissue is disclosed. The tissue is preferably autologous relative to the recipient of the graft and is conveniently prepared around or on a molding support inserted into a body cavity of the intended recipient of the graft. These tissues and methods are particularly useful in the treatment or prophylaxis of diseased or damaged blood vessels such as in atherosclerosis.

1 Claim, 17 Drawing Sheets

SILASTIC TUBING IN THE PERITONEAL CAVITY

OTHER PUBLICATIONS

Härtig et al. "Blot analyses and immunocytochemistry of neural antigens with digoxigenylated primary and secondary antibodies" *Brain Research Protocols* 2(1)35–43, 1997.

Kleinert et al. "The neointima formed in endothelial cell sodded ePTFE vascular grafts results from both cellular-hyperplasia and extracellular-hypertrophy" *Cell Transplantation* 5(4): 475–482, 1996.

Koch et al. "Analysis of 274 omniflow vascular prostheses implanted over an eight-year period" *Aust. N.Z.J. of Surg.* 67:637–639, 1997.

Kuo et al. "The potential of In Vivo vascular tissue engineering for the treatment of vascular thrombosis: a preliminary report" *Am. J. Reontgenol.* 171:553–558, 1998.

Manderson et al.: Venous response to endothelial denudation *Journal of Pathology* 18:77–87, 1986.

Puchkov et al. "Vascularization of human embryo neocortex in the rat eye anterior chamber immunosupressed by cyclosporine A" *Morfologia* 110(5):15–19, 1996.

Sappino et al. "Differentiation Repertoire of Fibroblastic Cells: Expression of Cytoskeletal Proteins as Marker of Phenotypic Modulations" *Lab. Investigation* 63:144–161, 1990.

Schwartz et al. "Subspecialty Clinics: Cardiology—Coronary restenosis: prospects for solution and new perspectives from a porcine model" *Mayo Clin. Proc.* 68:54–62, 1993.

Verhagen et al. "Thrombomodulin activity on mesothelial cells: perspectives for mesothelial cells as an alternative for endothelial cells for cell seeding on vascular grafts" *British Journal of Haematology* 95:542–549, 1996.

Walden et al. "Matched elastic properties and successful arterial grafting" *Arch–Surg.* 115(10):1166–1169, 1980.

* cited by examiner

SILASTIC TUBING IN THE PERITONEAL CAVITY

H&E STAINING

ALPHA ACTIN STAINING

IMPLANT MATERIAL

FIELD OF INVENTION

The present invention relates generally to tissue implant material for use in grafting procedures. More particularly, the present invention provides non-vascular tissue for use as vascular graft material. The present invention further contemplates a method of vascular grafting using non-vascular tissue. The tissue of the present invention is preferably autologous relative to the recipient of the graft and is conveniently prepared around or on a molding support inserted into a body cavity of the intended recipient of the graft. The tissues and methods of the present invention are particularly useful in the treatment or prophylaxis of diseased or damaged blood vessels such as in atherosclerosis.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

BACKGROUND

Tissue grafting represents a major advance in the medical treatment of diseased or damaged tissue. In some cases, tissue grafting represents the sole avenue of medical treatment. However, the success of tissue grafting depends on a range of factors including the availability of suitable donor tissue and the extent of immunological intolerance by the recipient.

An example of grafting is vascular grafting which is one approach in dealing with atherosclerosis. Atherosclerosis is the principal cause of heart disease, stroke and gangrene of the extremities. Atherosclerotic lesions are a result of an inflammatory response to a damaged artery wall and is associated with excessive lipid deposition (Schwartz et al, 1993). The development of atherosclerosis (atherogenesis) is complex and involves several cell types such as macrophages, T-cells and smooth muscle cells of the intima. Atherosclerosis is responsible for a high rate of mortality and an even higher rate of long term physical impairment of subjects affected by this disease.

A method of treating atherosclerosis is to insert bypass grafts around an artery blocked by plaques. The most common vascular graft material is saphenous vein or mammary artery from the patients. Such graft material is referred to as an autograft. Vein and artery autografts are flexible, viable, non-thrombogenic and compatible. However, while the mammary artery seldom develops atherosclerosis, it may not always be the proper size or length, and saphenous vein may have varicose degenerative alterations that can lead to aneurysm formation when transplanted to a high pressure arterial site. Furthermore, the non-thrombogenic surface of endothelial cells of saphenous veins is often damaged during graft preparation.

Similarly, the use of dialdehyde starch tanned bovine xenografts has been generally abandoned due to a high incidence of aneurysm formation and poor resistance to infection.

For these reasons and because autologous grafts not always available, attempts have been made to produce synthetic vascular prostheses. The first synthetic vascular prosthesis was made of Vinyon-N and was implanted into a patient in the late 1940's. The patient died 30 minutes after the operation. Replacements have been made with nylon, then later with TEFLON which is polytetrafluoroethylene manufactured by DUPONT and DACRON which is a long-chain polyester made from ethyleneglycol and tesephthalic acid manufactured by DUPONT. Nylon was found to lose most of its tensile strength after a brief period of implantation leading to aneurysmal dilation and graft rupture. Although both DACRON and TEFLON fabric grafts perform reasonably satisfactorily in high flow, low resistance conditions such as in the aorta, iliac and proximal femoral arteries, neither of these two materials is satisfactory for small caliber arterial reconstructions. Such grafts are compounded by graft failures from stenosis at the anastomic sites and excessive intimal hyperplasia. These complications are associated with graft thrombogenicity, poor healing and lack of compliance.

In the early 1970's, non textile vascular grafts prepared from expanded polytetrafluoroethylene (ePTFE) were introduced. ePTFE is the most chemically inert of all polymeric materials and is not degraded or changed in the chemical environment of the body and is extremely easy to suture. However, poor healing characteristics and lack of compliance are major causes for its lack of performance.

Indeed, the major problem with all synthetic vascular prostheses is that they are foreign bodies, so that blood coagulation can occur on their luminal surfaces causing occlusion in prostheses. One innovation designed to improve the patency of the synthetic vascular graft is to coat the lumen of the vascular graft with endothelial cells. While flow through the graft is improved and thrombogenesis reduced, graft failure can still occur due to occlusion by overgrowth of endothelial cells. In an attempt to control the growth, gene therapy has been used. This refinement addresses the overgrowth, but retrovirally transduced cells on the graft are not able to withstand the shear stresses encountered by flow of blood and are sheared off. Also, the procedure for obtaining endothelial cells from the patient is invasive and the cells are hard to propagate in vitro.

Tissue-polymer prostheses are available which incorporate a combination of tissue and synthetic material in the form of an integral composite. In one form, silicone mandrels covered with DACRON mesh are implanted beneath the cutaneous trunci muscles of sheep where they become encapsulated with ovine collagen (Koch et al, 1997). The tubes are then excised and trimmed of excess fat and connective tissue is then fixed with glutaraldehyde. The silicone mandrel is then removed leaving the fibre-reinforced tube which, after sterilization, is stored in ethanol (Edwards and Roberts, 1992). Although this prosthetic device has been successfully used, it does suffer the disadvantage of lacking elastin, an important component to prevent aneurysmal and dilatory changes from stretching both the collagen and mesh components. Further-more, the prosthetic device uses glutaraldehyde and this has the propensity to induce non-specific calcification of the implanted device.

In summary, despite considerable experimental and clinical research, none of the biological and synthetic grafts produced thus far is an ideal substitute for a blood vessel such as an artery, arterio-venous shunt or an access fistula. Limited availability, graft deterioration and complications such as thrombosis, aneurysm formation and excessive subintimal hyperplasia at the anastomotic sites are major problems.

There is a need, therefore, to develop tissue for use in vascular grafting which exhibits the biocompatibility of a recipient's own tissue but which is created artificially obviating the need to sacrifice existing, i.e. indigenous, tissue from the recipient. In accordance with the present invention, the inventors have identified a means of producing living graft issue for use as vascular tissue but which is derived from non-vascular tissue.

SUMMARY OF THE INVENTION

The present invention is predicated in part on the surprising observation that granulation tissue produced in a cavity of a live body in response to foreign material is useful as grafting material. The granulation tissue comprises non-thrombogenic, mesothelial (endothelial-like) cells overlying several layers of myofibroblasts which, in a preferred embodiment, is highly contractile, strong and responds to agonists and antagonists in a manner similar to smooth muscle in blood vessels. After grafting, elastic fibres are produced by the myofibroblasts.

Accordingly, one aspect of the present invention provides isolated tissue suitable for use in a vascular graft said tissue comprising granulation tissue produced on a molding support, and wherein the tissue is removed from the molding support prior to use.

Although this aspect of the present invention is directed to tissue suitable for use in vascular grafting, the present invention extends to the use of the non-vascular granulation tissue formed in a body cavity in any suitable graft. In a particularly preferred embodiment, the present invention provides living non-vascular tissue for grafting of substitute blood vessels.

Accordingly, another aspect of the present invention provides an isolated substitute blood vessel or a portion thereof comprising granulation tissue covered by non-thrombogenic mesothelial cells wherein the tissue forms on a molding support inserted into a body cavity of the intended recipient of the substituted blood vessel and wherein the tissue is removed from the molding support prior to use.

In one embodiment, the substitute vessel is a substitute for an artery.

In another embodiment, the substitute vessel is a substitute for an arterio-venous shunt or an access fistula.

Reference herein to "prior to use" means that prior to the tissue being used in a vascular graft, such as a substitute blood vessel, it is removed from the molding support. This may occur immediately prior to grafting or a period of time before grafting.

In a particularly preferred embodiment, the substitute artery is prepared in vivo by inserting a molding support in the form of a tube into a cavity of a live body and maintaining the molding support in vivo until such time as granulation tissue forms on and around the molding. The granulation tissue takes the form of the shape of the molding. The molding support may, in fact, become encapsulated. Preferably, therefore, where the tissue is for use as a substitute artery, the molding is a hollow or solid tube with a desired length and diameter. The molding needs to provoke an inflammatory response. In this regard, in a preferred embodiment, the molding support is recognised by the recipient as a foreign body. The molding support may or may not need to be sterile.

Although not wishing to limit the present invention to any one theory or mode of action, it is proposed that peritoneal or other body cavity macrophages coat the molding support together with other cells of the immune system such as but not limited to cells involved in an immune-mediated inflammatory response. Cells proposed to be involved include granulocytes, macrophages and stromal cells. The macrophages eventually take on a flattened appearance, and fibroblasts cells as well as cells with an intermediate morphology appear. Eventually, a continuous layer of mesothelial cells and cells resembling myofibroblasts forms. The cytoplasm of these cells shows the abundant rough endoplasmic reticulum seen in normal fibroblasts but also contains massive but discrete bundles of microfilaments with dense bodies which closely resemble those of smooth muscle cells. This tissue is referred to herein as "granulation tissue". The molding support is then removed from the body cavity and separated from the cells and discarded. It may be necessary in order to separate the cells from the molding support to cut or sever parts or portions of the tissue. In the case of the preparation of a substitute artery, the molding is in the form of a tube and the tissue remaining after the tube is discarded is everted, i.e. turned inside out, such that the mesothelium lining the granulation tissue is now lining the inside of the substitute vessel thus mimicking the structure of a normal blood vessel. In this regard, the tissue generally encapsulates the tubular molding and needs to be cut at one or both ends in order for the molding to be separated from the tissue.

Accordingly, another aspect of the present invention provides an isolated substitute blood vessel or a portion thereof comprising a tubular tissue section comprising living myofibroblasts within granulation tissue wherein the tissue is formed on a tubular mold and then removed from the mold and everted.

Yet another aspect of the present invention provides an isolated tissue suitable for use in a vascular graft said tissue produced by the process of placing a molding support within a body cavity for a time and under conditions sufficient for granulation tissue to form on said molding support, removing the molding support from the cavity and then removing the tissue from the molding support and everting the tissue.

Still yet another aspect of the present invention contemplates a method of producing substitute tissue, said method comprising placing a molding support within a body cavity for a time and under conditions sufficient for granulation tissue comprising myofibroblasts to form, removing said molding support from the body cavity and separating the granulation tissue from said molding support.

In a particularly preferred embodiment, the present invention is directed to a method for producing a substitute blood vessel said method comprising inserting into a body cavity a molding support in the form of a tube for a time and under conditions for granulation tissue with myofibroblasts to form, removing the tubular molding from the body cavity, separating the tubular molding away from the granulation tissue and everting said granulation tissue.

Any body cavity may be used including but not limited to the peritoneum, thoracic cavity, scrotum, brain, joint or pericardial cavity. Preferably, the cavity is lined with mesothelial cells. The peritoneal cavity is the most convenient and least disruptive to the host and is preferred in accordance with the present invention.

The molding support may be surgically implanted into the body cavity where it is effectively placed without restraint in the cavity.

Alternatively, the molding support is fixed to a region within the cavity. This may make insertion and/or retrieval of the implant easier. For example, a molding support may be provided by way of a catheter. In this regard, a molding support such as a tubular molding can be provided to the peritoneal cavity, for example, via a prosthetic device such as a peritoneal dialysis catheter. One example of a peritoneal dialysis catheter is a Tenckhoff catheter. This provides a convenient manner in which to gain access to the molding in the peritoneum by a less invasive procedure than open surgical intervention. A catheter may be employed as a source of tubular molding per se, i.e. that piece of the catheter inserted into the cavity or the catheter may be used as a conduit for passing suitable molding supports into and out of the cavity.

Accordingly, another aspect of the present invention provides a prosthetic device which facilitates the provision of a molding support to a body cavity, said prosthetic device comprising an elongated member, said member having a portion adapted to be inserted into a body cavity and a portion adapted to be external to the body cavity wherein the portion adapted to be inside the body cavity comprises a molding support or permits entry of a molding support into said body cavity wherein granulation tissue forms on or around said molding support which granulation tissue is suitable for use as a vascular graft, such as substitute blood vessel.

In accordance with this embodiment, the internal portion of the elongated member of the catheter may be the molding support per se. Alternatively, the elongated member may be a hollow tube through which a molding support may be passed from the portion of the catheter external to the cavity to the portion of the catheter in the cavity. In the case of the latter embodiment, the molding support would preferably be extended past the terminal portion of the portion inside the cavity such that the molding support or part thereof is exposed to the cavity. Conveniently, a line or wire or other means is attached to one part of the molding support to facilitate retrieval of the molding support through the elongated member.

The portion of the member external to the body cavity may still be located inside the body but outside the lining of the body cavity. For example, the external portion may be positioned subcutaneously. Alternatively, the external portion is outside the body.

Preferably, the body cavity is the peritoneal cavity.

Preferably, the elongated member is a filament or tubular mold.

Another aspect of the present invention provides a filament or tubular mold support capable of acting as a catheter for a body cavity wherein one portion of said filament or tubular mold support is present in the body cavity and another portion of filament or tubular mold support is outside the body cavity.

In one embodiment, the prosthetic device or filament or tube is packaged for sale with instructions for use.

In one preferred embodiment, a Tenckhoff catheter or its functional equivalent is used. This may have a single or double cuff of DACRON to prevent migration of bacteria and, hence, peritonitis when used in the peritoneal cavity, and may be used with or without silicon discs to hold the omentum and bowel away from the tubing. Conveniently catheters are inserted into the peritoneal cavity over a guide wire through an incision, generally after first infusing with dextrose dialysis solution. The cuff is then sewn in place in the peritoneum and an adapter attached to the external portion of the catheter.

The present invention is particularly directed to the use of body cavities to prepare the substitute tissue. This is done, however, with the understanding that the present invention extends to preparing substitute tissue in vitro. For example, through tissue culture techniques including feeder layers, granulation tissue may be induced to form on or around a molding support. The use of in vitro culture techniques has an advantage in that culture conditions can be manipulated and controlled such as by the addition of, for example, growth factors and cytokines. It also has the advantage of not requiring an invasive procedure in order to produce the artificial artery. Generally, an artificial vessel is made in vitro with no artificial support scaffold but with a scaffold of matrix it has created itself, as with the mesothial-lined granulation tissue tube formed in a body cavity of a host. The production of artificial vessels in vivo and in vitro both have advantages and both techniques are contemplated by the present invention.

The molding support is selected depending on the intended use of the tissue. For example, tubes, beads or discs may be used. Tubes are used for the preparation of substitute blood vessels. Discs and beads may be used for repairing internal organ or tissue damage.

The molding support may be any material including polymers such as cellulose, polyacrylamide, nylon TEFLON, DACRON, polystyrene, polyvinyl chloride, polypropylene, silastic tubing and polytetrafluoroethylene. The use of glass is also contemplated by the present invention but is not a preferred molding support. Reference to "tubular molding" is not to be taken as limiting the molding to a hollow tube. The present invention also contemplates a molding support in the form of a filament such as a solid fibre. Up to the present time, plastic silastic tubing is the most useful form of molding support for the preparation of substitute blood vessels.

In a particularly preferred embodiment, the present invention contemplates a method for producing a substitute blood vessel said method comprising inserting a molding support in tubular form into the peritoneal cavity of a recipient for a time and under conditions sufficient for granulation tissue to form with myofibroblasts, removing the molding from the peritoneal cavity, separating the molding away from the granulation tissue and everting said granulation tissue.

Preferably, the molding support is silastic tubing or its equivalent. The length and diameter of the substitute blood vessel is determined by the length and diameter of the tubing employed as the molding support. Conveniently, the diameter of the tubing may range from about 0.1 mm to about 10 mm and more preferably from about 0.5 mm to about 5 mm. The length of the tubing will depend on the amount of graft required and on the size of the body cavity. For example, a length of from about 0.1 mm to about 1000 mm, more particularly from about 1 mm to about 800 mm and even more particularly from about 3 mm to about 500 mm may be employed. More preferably, the length is from about 10 mm to about 250 mm. In addition, this procedure permits branched or looped tubing being employed to generated branched or looped blood vessel grafts.

The method of the present invention is particularly useful for generating substitute blood vessels since the substitute blood vessels of the present invention exhibit a non-thrombogenic surface, have compliance and elasticity, exhibit long-term tensile strength, are biocompatible, are easy to handle and have suturability and are available in any size depending on the size and shape of the tubular molding. The tubular molding may also comprise spiral grooves. The spiral orientation of smooth muscle cells in blood vessels facilitates control of compliance.

The preferred recipient for the implantation of the molding support is the patient requiring the substitute blood vessel or transplant. However, it is within the scope of the present invention for substitute blood vessels or other transplantable tissue to be prepared in other individuals such as genetically related individuals or non-related individuals. In the case of the latter, immune-suppressing therapy may be required to effect the transplant.

The present invention is particularly directed to grafting in humans although the subject invention extends to other animals and birds such as primates, laboratory test animals (e.g. mice, rats, rabbits, guinea pigs), livestock animals (e.g. cows, sheep, pigs, horses, donkeys), companion animals (e.g. dogs, cats), captive wild animals, caged birds, game birds and poultry birds (e.g. chickens, geese, ducks, turkeys).

The present invention further contemplates the genetic manipulation of the substitute tissue. In one embodiment, once the tissue is removed from the body cavity, the mesothelial cells are transfected with a viral vector, naked DNA or other suitable genetic vehicle. Alternatively, or in addition, the myofibroblasts may be genetically manipulated. Generally, the aim of genetic manipulation is to introduce traits which facilitates function or operation of the graft. For example, genes encoding tissue plasminogen activator (tPA), urokinase plasminogen activator (uPA) or streptokinase may be introduced. Alternatively, or in addition, genes may be introduced such as which encode nitric oxide synthase (NOS) which prevents unwanted clotting and spasm.

The present invention further contemplates a method of treating atherosclerosis or other blood vessel disease said method comprising by-passing or replacing the damaged blood vessel by grafting a substitute blood vessel, said substitute tissue comprising myofibroblasts within granulation tissue.

Preferably, the substitute blood vessel is prepared by placing a molding support comprising a tube in a cavity of a live body, such as a peritoneal cavity, for a time and under conditions sufficient for granulation tissue comprising myofibroblasts covered by mesothelium to form, removing said molding from the body cavity and separating the molding away from the granulation tissue and then everting the granulation tissue.

Yet another aspect of the present invention provides an isolated tissue suitable for use in a vascular graft said tissue produced by the process of placing a molding support within a body cavity for a time and under conditions sufficient for granulation tissue to form on or around said molding support and wherein the tissue is removed from the molding support prior to use.

Preferably, the tissue is suitable for use as a substitute blood vessel or a portion thereof, in which case the molding support is in tubular form.

Preferably, the granulation tissue is covered by non-thrombogenic mesothelial cells. The granulation tissue generally comprises living myofibroblasts within granulation tissue. The living myofibroblasts produce elastic fibres within a few weeks of transplantation to a high pressure arterial site. Elasticity is important to prevent aneurysmal and dilatory changes.

The present invention further provides an isolated substitute blood vessel maintained in a frozen state for use by a mammal in which it is produced said substitute blood vessel formed by placing a tubular molding within a body cavity of said mammal for a time and under conditions sufficient for granulation tissue comprising myofibroblasts to form, removing said tubular molding and separate granulation tissue away from the tubular molding and then everting the granulation tissue.

Preferably, the body cavity is the peritoneal cavity.

Still another aspect of the present invention contemplates the use of a molding support in the manufacture of tissue suitable for use in a vascular graft, said tissue comprising granulation tissue produced on said molding support.

The present invention is now described with respect to the practice of one particular preferred embodiment. The following description is in no way intended to limit the scope of the instant invention.

To prepare a substitute blood vessel, an approximately 20 to 100 mm long piece of approximately 1 to 10 mm diameter silastic tubing comprising spiral grooves is optionally coated with fibronectin which enhances macrophage adhesiveness. The tube is placed in the peritoneal cavity and 10 to 15 ml of balanced salt solution and dextrose added together with a growth factor or cytokine such as but not limited to granulocyte-macrophage colony-stimulating factor (GM-CSF) in order to stimulate macrophage recruitment and proliferation.

The peritoneal cavity is closed and in approximately 1 to 6 weeks and more preferably 2 to 3 weeks later, the tube is removed from the cavity. It is necessary to remove the tissue from the tube by a process of eversion. Generally, the ends of the tissue are cut, the tubing removed and discarded and one end of the tissue held by five forceps inserted through the lumen. The tissue is pulled back through the lumen, completely turning inside out. Generally, heparin is then infused through the everted tissue at the time of grafting into a blood vessel.

The present invention is further described by the following non-limiting Figures and Examples.

c $1 \times 10^{-9}$M phenylephrine
d $3 \times 10^{-9}$M phenylephrine
e $1 \times 10^{-8}$M phenylephrine
f $3 \times 10^{-8}$M phenylephrine
g $1 \times 10^{-7}$M phenylephrine
h $3 \times 10^{-7}$M phenylephrine
i $1 \times 10^{-6}$M phenylephrine
j $3 \times 10^{-6}$M phenylephrine
k $1 \times 10^{-5}$M phenylephrine
l $3 \times 10^{-5}$M phenylephrine
m $1 \times 10^{-4}$M phenylephrine.

Figure 13A:

FIG. 13A is a photographic representation of a rabbit granulation capsule around silastic tubing prior to transplantation.

Figure 13B:

FIG. 13B is a photographic representation of rabbit granulation tissue after fixing and removal of the silastic tubing. The tissue has been trimmed.

FIG. 14 is a photographic representation showing:

a. transverse section of a 10 mm tube of two week granulation tissue four months after it had been grafted by end to end anastomoses into the abdominal aorta of the same rat Note the thickened "adventitia". Haematoxylin and eosin. X30.

b. α-Smooth muscle actin staining (dark) of myofibroblasts in a 20 mm tube of two week granulation tissue formed in the rabbit peritoneal cavity, four months after it had been grafted by end to end anastomoses into the carotid artery of the same animal. Note small blood vessels in "adventitia". X100.

c. Wall of 20 mm tube of two week granulation tissue formed in the rabbit peritoneal cavity, four months after it had been grafted by end to end anastomoses into the carotid artery of the same animal. Stained with antibodies to smooth muscle myosin heavy chain (dark). X150.

d. Wall of 10 mm tube of two week granulation tissue formed in the rat peritoneal cavity, four months after it had been grafted by end to end anastomoses into the abdominal aorta of the same rat. Stained with Weigert's elastic stain. Note elastic fibrils. X300.

EXAMPLE 1

Creation of an Artificial Blood Vessel

The first step in creating an artificial blood vessel was to determine an appropriate implant material which would:

(i) initiate granulation tissue development;
(ii) be covered by mesothelium;
(iii) form a tube-like structure;
(iv) be of variable diameter and length;
(v) not attach to omentum/mesentery in the peritoneal cavity; and
(vi) allow its own easy removal from the granulation tissue.

The second step was to determine its optimal time for harvest.

a) Selection of appropriate material as an arterial template

Figure 1:
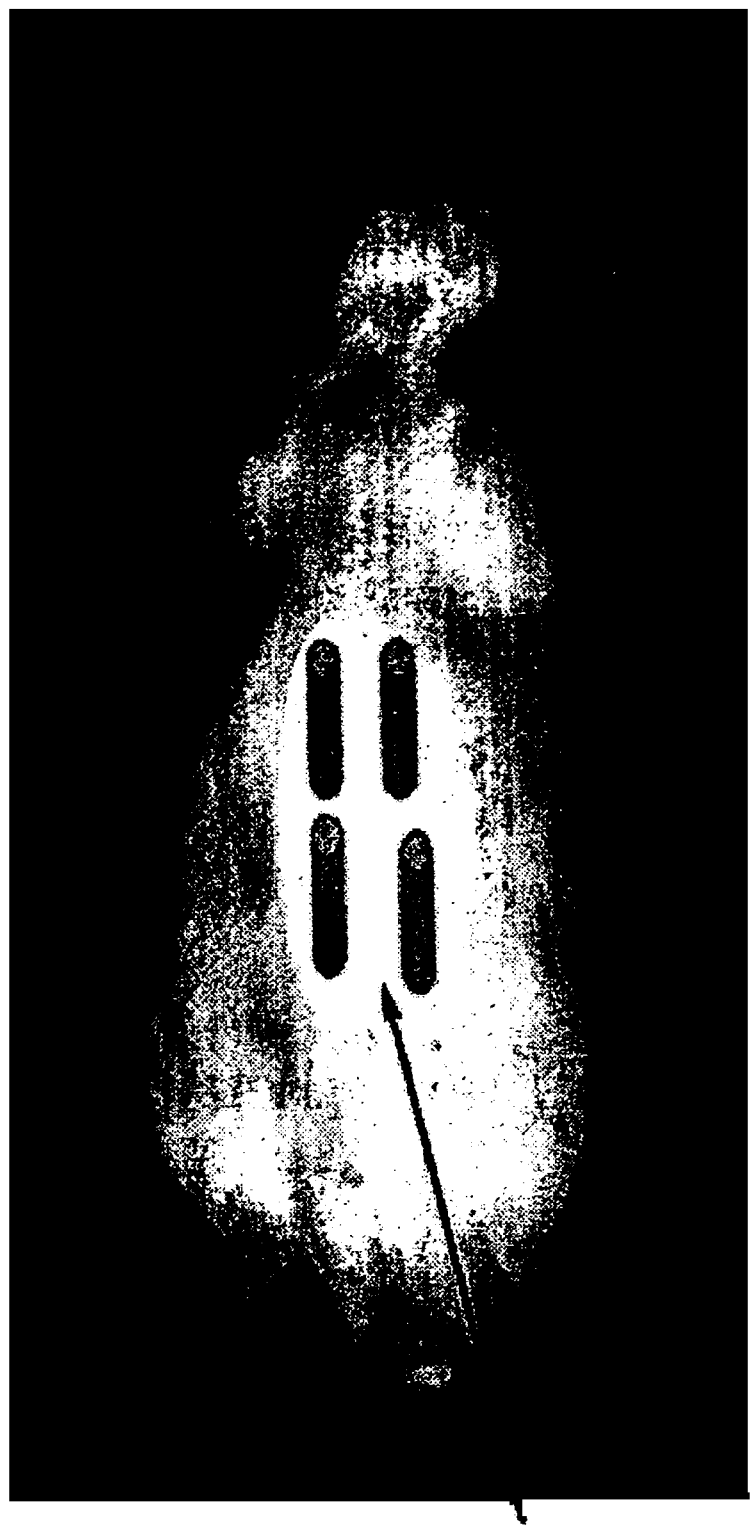
FIG. 1 is an illustration of molding support positioning in the rat peritoneum.

Twenty male adult Wistar rats were anaesthetized with 2.5% v/v ($O_2$) halothane. A 20 mm incision was made in the shaved abdominal wall and a variety of objects—plastic silastic tubing (inner diameter range from 0.5–5 mm), glass rod, expanded polytetrafluroethelene (ePTFE) graft (inner diameter 5 mm) and Dacron graft (inner diameter 6 mm)—inserted inside the peritoneal cavity (see FIG. 1) then the incision closed by 8 interrupted sutures (10-0 Dexon silk). For comparison with previous studies, 10 ml boiled (rabbit) blood clot was inserted into some rats. Only one type of object was used per animal. Animals were divided into four groups (labelled Groups 1 to 4) corresponding to the length of time the foreign body remained inside the peritoneal cavity (Weeks 1 to 4, respectively).

When a boiled blood clot was placed inside the peritoneal cavity, the majority of the clot was reduced to a single ball suspended within the peritoneal cavity. The granulation tissue appeared as a circumferential and organised layer of myofibroblasts on the outer surface of the clot.

Glass pipettes were found to be less suitable templates for artificial arteries since rats implanted with glass frequently had complications leading to death.

Dacron graft was also found to be not preferred as no organized pattern was found around the graft. Instead, there was a rather a haphazard-like arrangement that penetrated the graft material making it difficult to remove from the granulation tissue without tearing the tissue. When ePTFE graft was implanted into the peritoneal cavity highly organized concentric layering of collagen and α-actin positive cells occurred. The main drawback with the ePTFE graft was the ease with which it adhered to peritoneal fat bodies (omentum/mesentery). Subsequently, a high degree of vascularization was found on these grafts. As it was critical for this study for the material to remain floating at all times, these grafts were rejected. As with the Dacron, difficulty also arose during separation of the granulation tissue from the ePTFE graft, with large tears often occurring.

Figure 2:
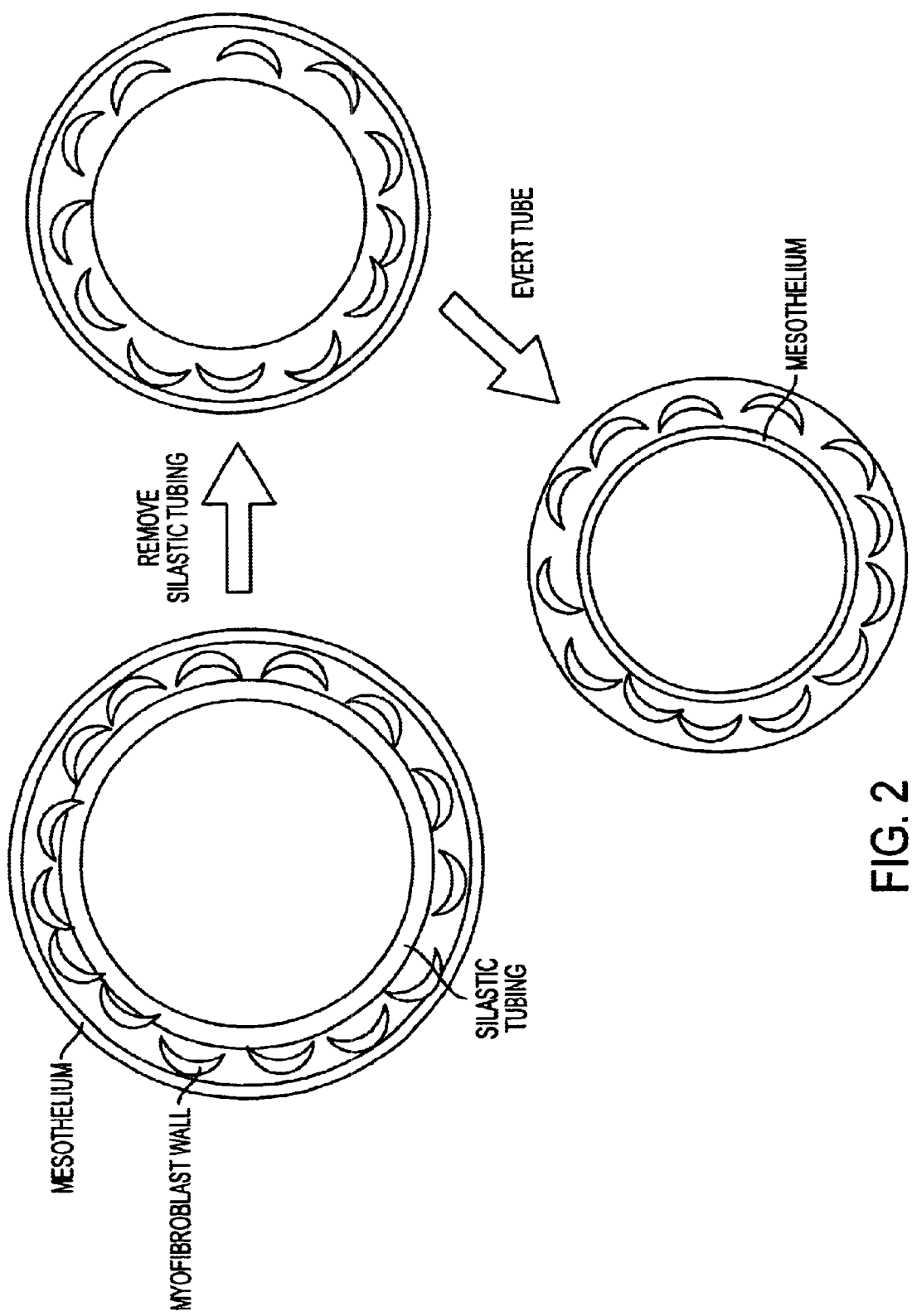
FIG. 2 is a diagrammatic representation of a cross section of a granulation (myofibroblast) tube showing the tube as it appears on removal from the body cavity with inner silastic tubing covered by layers of myofibroblasts and collagen and coated with a single layer of mesothelium; the tube following removal of silastic tubing; and the everted tube of living granulation tissue with mesothelium lining the inside of the living tube, forming a structure resembling an artery.

The plastic silastic tubing was found to be the most effective material as it had a greater than 35% rate of remaining afloat over the experimental period. Close to the tubing there was a layer of connective tissue covered by a layer of cell-rich granulation tissue. Mesothelium formed an outer lining of the myofibroblast capsule. This mesothelial layer is extremely important as it possesses fibrinolytic and anti-coagulant activity (Verhagen et al, 1996). The silastic tubing was also the easiest to remove from the granulation tissue, with little to no damage done during harvesting. Most importantly, the tube-like structures of diameter 0.5 to 5 mm could be easily everted such that the mesothelium now lined the lumen. This created a tubular structure that mimics the structure of a normal blood vessel, with an inner "endothelium", "media" of smooth muscle-like cells and outer "adventitia" of connective tissue (FIG. 2). The fact that tubes of such small diameter are producible is especially important since synthetic grafts are not suitable to replace vessels of small calibre as their thrombogenic surface can lead to occlusion.

(b) Optimal time for harvest

Upon establishing the right material to be used for this study, the optimal time for harvest was investigated. This was performed by homogenization of the tube followed by Western-blot analysis to determine the amount of smooth muscle mactin protein in the granulation tissue at various times. The level of α-actin provides an indication of the number and degree of differentiation of myofibroblasts present in the granulation tissue.

After one week, the smooth muscle α-actin protein level was close to that in the abdominal aorta (97% of that in abdominal aorta), however, there was a variable thickness in granulation tissue. After two weeks, there was uniform thickening of the graft and the α-actin level was at its highest (106%). After three weeks, the level of α-actin had decreased considerably (50%) compared to two weeks, post implant tissue. Histologically, there were few myofibroblasts present in the graft. After four weeks, there was the same amount of α-actin level as in the third week post implant (46%), with relatively few myofibroblasts and a thick capsule of connective tissue.

Therefore, the optimum time for the graft to be harvested from rat peritoneal cavity is 2 weeks post implantation. This ensures sufficient myofibroblasts are present within the granulation tissue to make a highly responsive wall against the high blood pressure encountered following transplantation of the everted tube of tissue into the arterial system.

EXAMPLE 2

Myofibroblast Tubes can be Grown to Different Lengths and in Different Species

Having established that silastic tubing is a suitable mould to produce a myofibroblast tube, that tubes of different diameter (0.5 to 5 mm) could be produced, and that 2 weeks is the optimal period for their development within the peritoneal cavity, the inventors next determined whether artificial arteries could be produced in a species other than the rat, and whether these vessels could be longer.

Four pieces of silastic tubing with outer diameter of 3 mm and length 10 mm (rat) and 5 mm by 20 mm (rabbit) were placed inside each animal. Five male Wistar rats and five male New Zealand White Cross rabbits were used. Two weeks after graft placement, animals were sacrificed. The silastic tubing was carefully removed and the tube of tissue gently everted such that the mesothelial layer now lined the inside of the freed myofibroblast tube. Segments of the four myofibroblast tubes (free-floating) from each animal were processed for transmission electron microscopy and light microscopy (Manderson and Campbell, 1986), while total protein was extracted for Western Blot analysis (Hartig et al., 1997).

Rat aortae were used as control for the Western blot analysis and volume fraction of myofilaments (Vvmyo) and for the staining with labelled antibodies against cytoskeletal markers and contractile filaments. Densitometry was performed on these bands from both the 2 week myofibroblast tube and rat aorta to obtain a quantitative measure of the amount of protein present with the aid of the Mocha image analysis system (Jandel Scientific). The bands were converted to values between 0–255, depending on their intensity. The more dense and intense the band, the closer the value to 0 and the lighter and less dense the band the closer the value to 255. For each protein the results were expressed as myofibroblast tube protein relative to aorta % (see Table 1). All statistical analyses were performed using the statistical software package 'SIGMA STAT' (Jandel Scientific, Calif., USA). Comparison of data from Vvmyo studies was carried out with the paired Student's t-Test. In all statistical analyses, a p value of less than 0.05 was considered significant.

Figure 3A:
FIG. 3 is a photographic representation showing A. Haemotoxylin and Eosin (H&E) staining and B smooth muscle α-actin (dark) staining of the rat myofibroblast tube after eversion.
Figure 3B:
Figure 4:
FIG. 4 is a photographic representation of a transmission electronmicrograph of two mesothelial cells lining the lumen and myofibroblasts in the wall of the tube.
Figure 5:
FIG. 5 is a photographic representation of a low power transmission electronmicrograph of the full thickness of rat granulation tissue. Note mesothelial cell lining the lumen (left) and spindle-shaped myofibroblasts throughout the wall.
Figure 6:
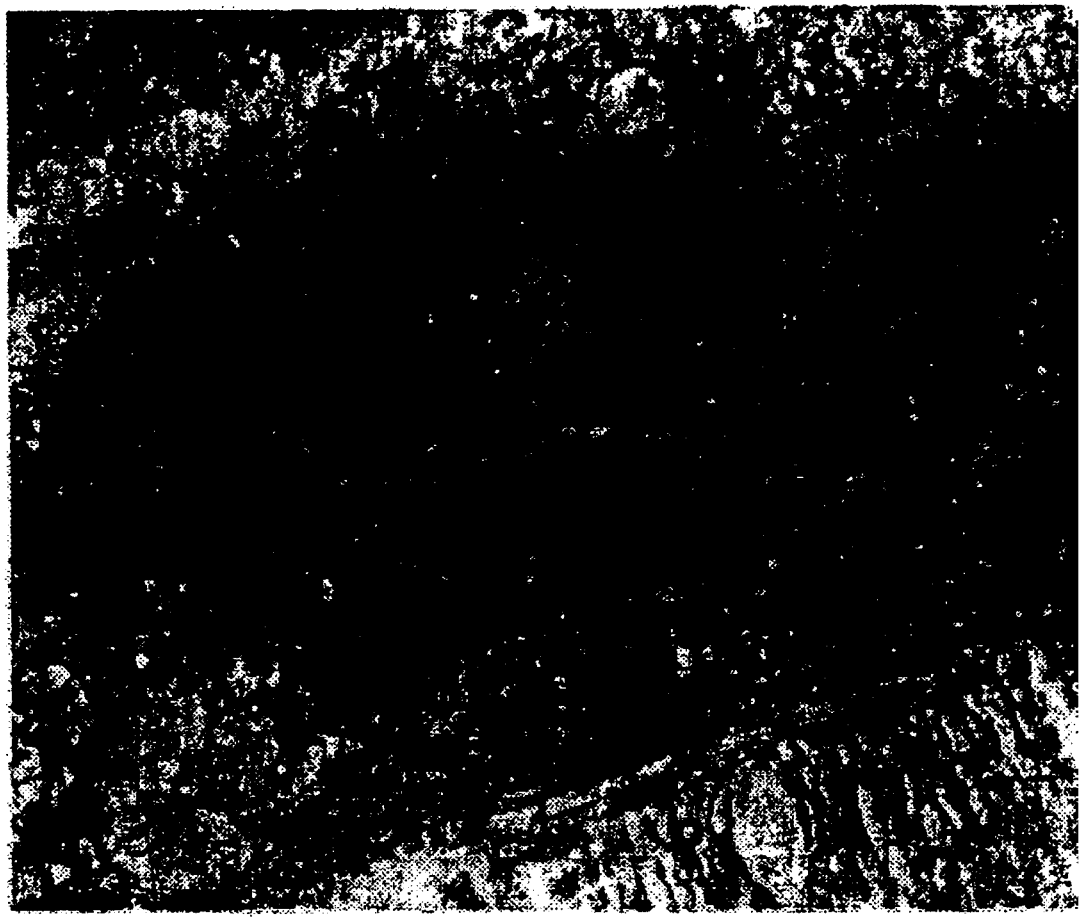
FIG. 6 is a photographic representation of a transmission electron micrograph of a macrophage within the rat myofibroblast tube.

Haematoxylin and Eosin staining of both rat and rabbit tubes showed a concentric layering of collagen bundles and spindle-shaped cells which were mactin positive (FIG. 3). The inside lining of these tubes was covered with a single layer of cells that stained positively for von Willibrand Factor (Serotec). Transmission electron microscopy confirmed the presence of mesothelial cells lining the inside of the myofibroblast tube (FIG. 4). In the outer region of the wall (which had been in contact with the silastic tubing), there was a layer of matrix with a single layer of myofibroblasts. In the mid-portion of the tube, cells at different stages were observed. Most cells were spindle shaped (FIG. 5). These cells had the characteristic of myofibroblasts with a folded nucleus indicating that they undergo contraction. Large amounts of synthetic organelles were present together with abundant focal/dense bodies of contractile filaments. There were also cells that closely resembled differentiated smooth muscle (FIGS. 4 and 5). The Vvmyo in the cells of the rat myofibroblast tube was $35.7\% \pm 1.6\%$ compared with $63.7\% \pm 5.7\%$ ($p<0.05$) for smooth muscle cells in the aorta of the same animals. Macrophages, readily distinguished by their irregular shape and high vesicle content, were commonly seen around the edge of the tube (FIG. 6). Western analysis also showed a relatively large number of ED1 positive cells (marker for macrophage) in the myofibroblast tube compared with the aorta.

Using cytoskeletal markers, Gabbiani and colleagues (see Sappino et al, 1990; Desmouliere et al, 1995) described five different phenotypes of myofibroblast: V type (vimentin positive), VA type (vimentin & mactin positive), VD type (vimentin & desmin positive), VAD type (vimentin & α-actin & desmin positive) and VADM type (vimentin, α-actin, desmin and myosin positive) cells. It was considered that V type cells resembled typical mesenchymal cells and VD cells corresponded to fibroblasts. The VADM type was considered to have differentiated into smooth muscle while the VAD type was associated with myofibroblasts. The myofibroblasts of the present invention expressed both vimentin and desmin and large amounts of α-actin and β-actin. Thus, by these criteria, the cells in the implant are myofibroblasts, but tending towards smooth muscle. The myofibroblast tube also contained smooth muscle myosin heavy chain (a marker of smooth muscle), but this was considerably less than in the aorta (Table 1).

The myofibroblast tube contained a similar amount of collagen Type I and IV as the aorta (Table 1). Fibres of collagen Type I tend to be quite flexible and are strongly cross-banded, which makes it an ideal connective tissue. Collagen Type IV is present within the basal lamina and is important in forming a cell's anchorage to the main skeleton of the structure. Therefore, the collagen framework of the myofibroblast tube provides considerable stability and strength. The low level of elastin indicates that the myofibroblast tube is more similar to a muscular artery than an elastic artery.

Thus, myofibroblast tubes of different diameter and length can be produced, and in species other than the rat, which fulfill the 6 required criteria for artificial arteries as outlined in Example 1 above. The myofibroblast tubes have a marker indicative of macrophages (ED1), as well as markers consistent with myofibroblasts differentiating towards vascular smooth muscle. However, from these experiments it was not clear whether the myofibroblasts are actually derived from peritoneal macrophages and whether they can be induced to differentiate further.

EXAMPLE 3

Figure 7A:
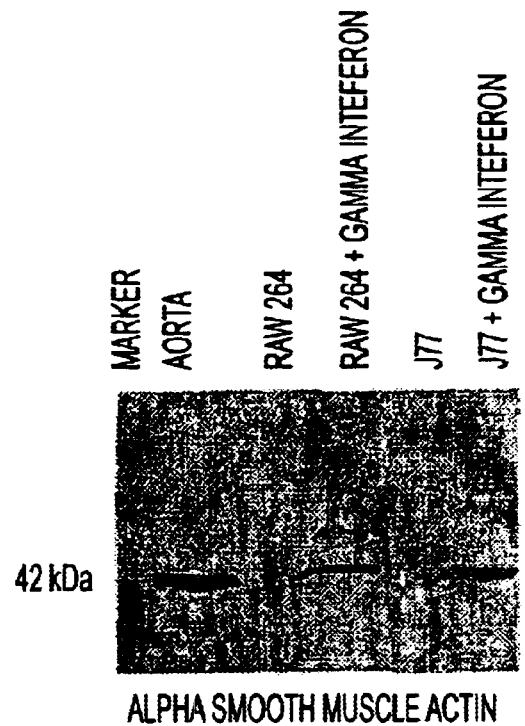
FIG. 7 is a photographic representation showing A. Western blot for smooth muscle α-actin in the presence and absence of γ-interferon. B. Staining for α-actin in RAW 264 and J774 macrophages treated with γ-interferon.
Figure 7B:
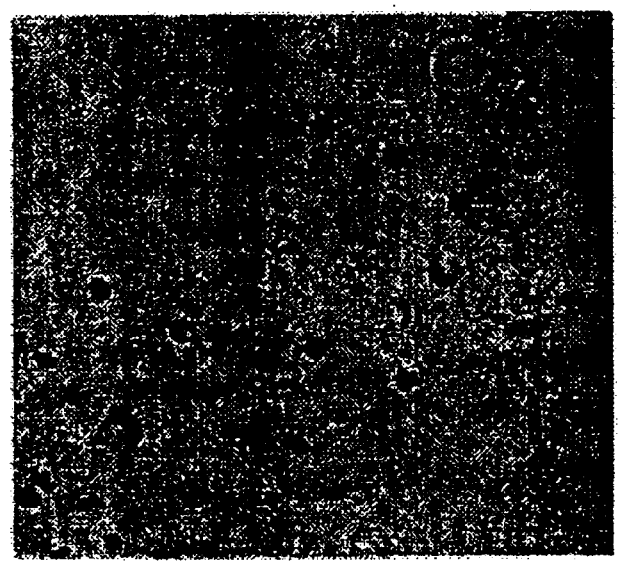

Macrophages Are the Source of Myofibroblasts/ smooth Muscle in the Peritoneal Tubes of Tissue a) In vitro studies Cultures of macrophage cell lines (RAW 264 and J774) were grown in Dulbecco's Modified Essential Medium (Gibco) and 10% v/v foetal calf serum at 37° C. in 6% v/v $CO_2$ humidified incubators. At sub-confluency, 25 U/ml of γ-interferon (Holan Biotechnology) was added to the macrophages and incubated for 16 hours. This cytokine caused de novo expression of SM α-actin proteins in both the RAW 264 (16%) and J774 (13.5%) macrophages, as measured by Western blotting (Hartig et al, 1997) [FIG. 7].

This experiment indicates that γ-interferon induces pure populations of macrophages to express the smooth muscle contractile protein α-actin, which is not normally expressed by these cells. Thus, it may be possible for macrophages to be a source of cells containing contractile protein under certain inflammatory conditions.

(b) In vivo studies

Figure 8:
FIG. 8 is a photographic representation showing in situ hybridization using DIG-labelled Y-chromosome probe showing positive cells in the wall of the myofibroblast capsule formed in the peritoneal cavity of an X-irradiated female mouse transfused with male bone marrow cells.

Definitive proof that cells of haemopoietic origin (as are peritoneal macrophages) are the source of myofibroblasts in the peritoneal tubes was shown by the following in vivo experiment: Female mice of the C57BL6 strain expressing the Ly 5.1 antigen on the surface of cells of haemopoietic origin were X-irradiated (9Gy) to destroy all bone marrow then immediately transfused with $10^6$ bone marrow cells taken from the femur of male C57BL6 mice of a congenic strain with haemopoictic cells expressing the Ly 5.2 antigen. Flow cytometry showed that there was greater than 80% repopulation of the donor (Ly 5.2) cells by 4 weeks. Into the peritoneal cavity of the host female mice was then placed a boiled blood clot or small piece of silastic tubing upon which a capsule of granulation tissue formed within a few days. Staining with antibodies to the Ly 5.2 antigen showed that the α-actin positive cells of the capsule were derived from the donor and thus of haemopoietic origin. This was further substantiated by their positive in situ hybridization with a probe for Y chromosome, proving their source is male, and thus of donor bone marrow origin (FIG. 8).

EXAMPLE 4

Myofibroblasts within Graft Walls can Differentiate Further Towards Smooth Muscle Cells In the normal artery wall, smooth muscle cells arc responsible for maintenance of vascular tone via contraction-relaxation and the cytoplasm of the cells is filled with myofilaments. However, following injury to the artery wall, the smooth muscle cells are responsible for restoring vascular integrity through their proliferation and synthesis of extracellular matrix. To do this, the smooth muscle cell loses its contractile ability (and contractile filaments) as the cytoplasm becomes filled with organelles involved in synthesis such as rough endoplasmic reticulum and free ribosomes. That is, the cells temporarily lose the appearance of differentiated smooth muscle cells and become more fibroblastic in structure and function. This is called modulation of phenotype (Campbell et al, 1989).

Fibroblasts are also able to modulate their phenotype in response to external cues. For example, during continuous tissue reorganization processes such as in the ovarian follicles, pulmonary septa, intestinal mucosa and during wound healing, fibroblasts express contractile proteins such as α-actin and at these times the fibroblasts are said to have differentiated into myofibroblasts.

The inventors investigated whether environmental factors affect the phenotypic (or differentiation) state of the macrophage-derived myofibroblasts which comprise the granulation tissue tubes formed in the peritoneal cavity in response to silastic tubing.

a) Neuronal influences do not affect the differentiation of macrophage-derived myofibroblasts Structures which are implanted into the anterior eye chamber become revascularized and reinnervated by the surrounding nerves of the host (Puchkov et al, 1996). Under these conditions, various developing tissues such as embryonic rat heart, fetal skin and adrenal medulla develop into their functional adult form.

To assess whether innervation induces further differentiation of macrophage-derived myofibroblasts, pieces of myofibroblast tube were transplanted to the anterior eye chamber of the rat from which it was harvested. Two week old myofibroblast tubes were removed from the peritoneal cavity of 12 Wistar rats under anaesthesia as earlier described. Segments of 1–2 mm in diameter and 5 mm in length were placed in phosphate buffered saline ready for the implantation. The eye of the same animal in which the myofibroblast tube was grown was carefully rinsed with distilled water and a drop of atropine applied to dilate the pupil. With the aid of a dissecting microscope, the cornea was penetrated obliquely with a specially prepared razor blade. The graft was inserted into the anterior eye chamber with sterile watchmaker forceps away from the pupil.

At termination (2 months post implantation) the rats were perfusion-fixed with 4% v/v glutaraldehyde via the left ventricle. The eyeball was dissected out and the implants were removed. Staining of the myofibroblast graft with sucrose-phosphate-glyoxylate (SPG) showed the majority of the innervation occurred along the periphery of the graft. There were signs of cell death (pyknotic nuclei) in and around the transplant, and most of the bulk of the wall consisted of collagenous matrix.

Contrary to expectation from previous studies with undifferentiated tissue, there was no significant change in the volume fraction of myofilaments (Vvmyo) of the cells (33.3+2.7% compared to 35.9+2.3%, p>0.05, in the non-transplanted myofibroblast tube). This indicates that innervation does not induce further differentiation of macrophage-derived myofibroblasts towards smooth muscle.

Figure 9A:
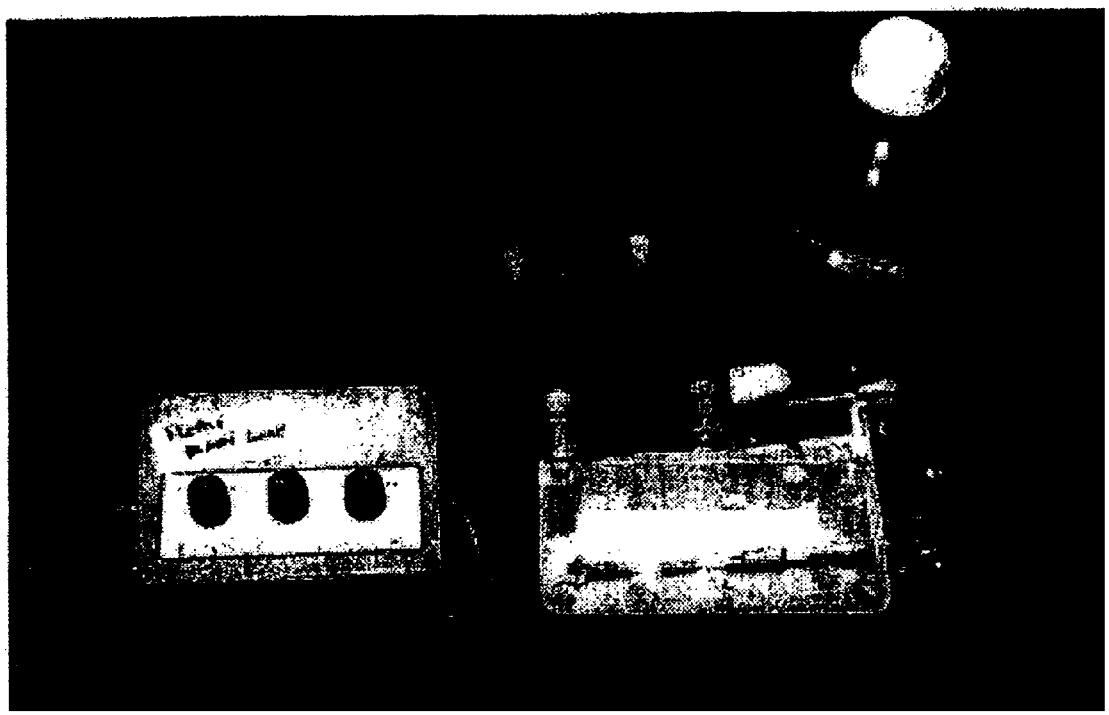
FIG. 9 is a photographic representation showing A. Apparatus for graft stretching. B. Higher power showing grafts attached to hooks in stretching apparatus.
Figure 9B:
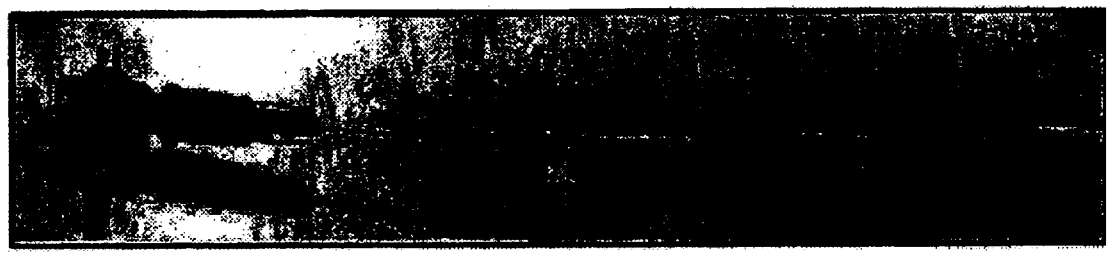

(b) Mechanical factors such as active stretching lead to further differentiation of macrophage-derived myofibroblasts Two week old pre-implant myofibroblasts were obtained from the peritoneal cavity of male Wistar rats. Under sterile conditions they were attached to the sterilized stretching apparatus (FIG. 9). At either end of the chamber are hooks (made from a syringe) to which the graft is attached. The hook closer to control box contains a retractile coil, which can be set to different frequency and amplitude, while the opposite end remains stationary. The culture medium was added to the chamber with the graft attached to the recoiling device. The whole chamber was placed inside the incubator (37° C.) and the graft underwent continuous stretching for 3 hours, 24 hours and 72 hours. The graft was stretched 50 times per minute to 105–110% of its resting length. At the end of the experiment the grafts were prepared for morphometric analysis of Vvmyo.

No signs of damage were observed while the graft underwent stretching. At the beginning of each stretching experiment, the myofibroblasts were located in random direction within the graft wall. Between 3 and 24 hours stretching, the myofibroblasts aligned themselves along the direction of the stretch and remained in this position following 72 hours of stretching. Most of the cells appeared to be more spindle and narrow compared to the control (pieces of the same grafts that were not stretched). Mural thickening could be seen at 72 hours of stretching, mostly composed of collagenous matrix.

No significant increase in the mean % Vvmyo was seen in 3 hours post stretching (44.5+6.1% compared with control in this experiment, 42.3+3.4%). However, the Vvmyo was significantly higher ($p<0.05$) following 24 hours of stretching (58.3+4.2%). At 72 hours post-stretching, the amount of myofilaments was reduced (48.8+3.9%) and replaced with large amounts of rough endoplasmic reticulum consistent with the observed increase in collagenous matrix.

From this study, the inventors conclude that cyclic and directional stretching stimulate the myofibroblasts to realign in the direction of the longitudinal strain and differentiate further towards contractile cells (mature smooth muscle). As the stretching continues, the myofibroblasts need to secrete additional collagen into their matrix to strengthen the graft and accommodate changes to their environment. They thus modulate back towards a "synthetic" cell in a similar way that vascular smooth muscle does in response to challenge to vessel wall integrity (see earlier).

EXAMPLE 5

The Myofibroblast Tube as an Autologous Vascular Graft (Artificial Artery)

Figure 10A:
FIG. 10 is a photographic representation showing: (A) insertion of an artificial artery into a rabbit carotid artery prior to releasing the clamps to permit blood flow; (B) an artificial artery functioning in a rabbit carotid artery under pressure.
Figure 10B:
Figure 11:
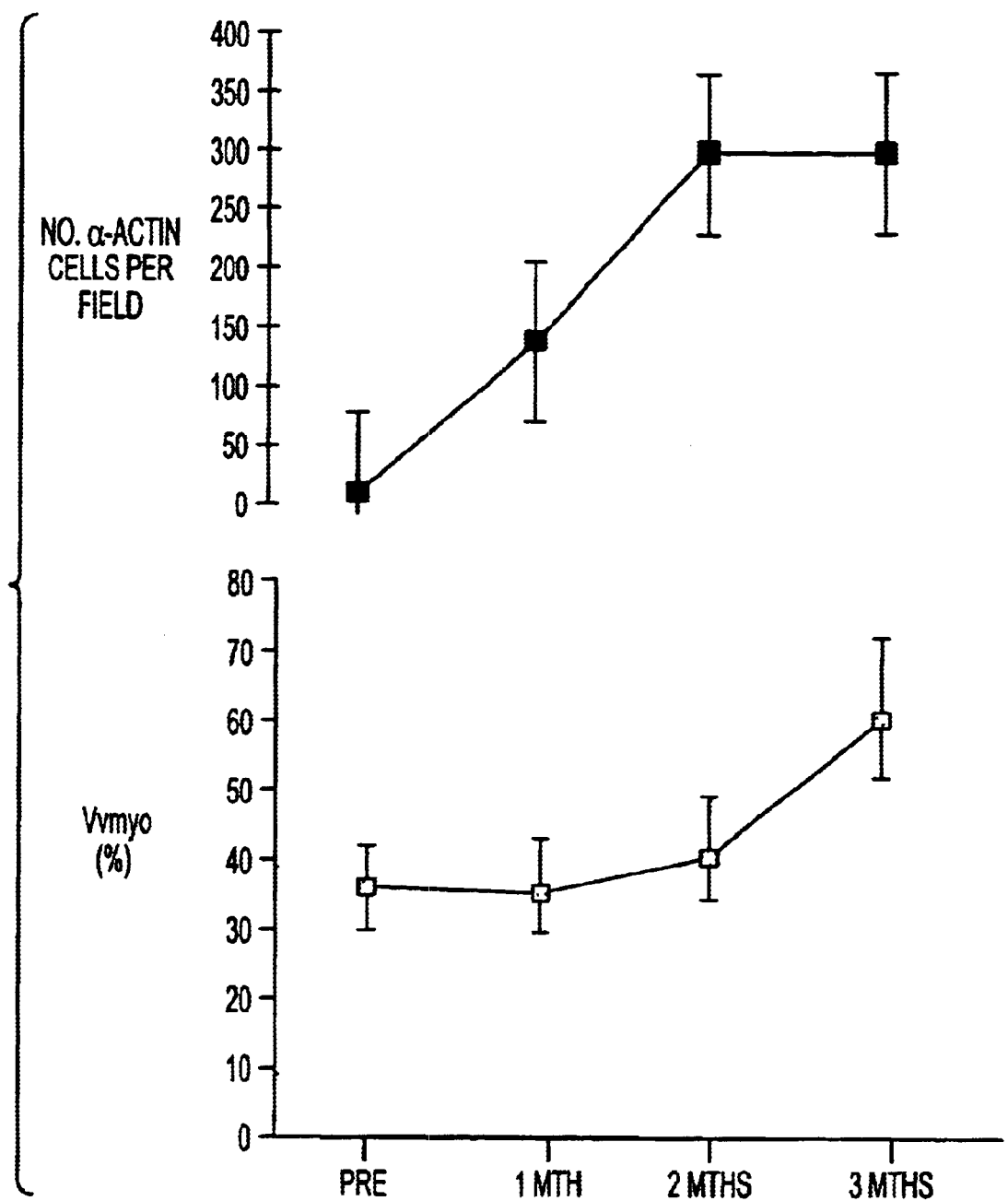
FIG. 11 is a graphical representation showing the number of α-actin staining cells and their Vvmyo within myofibroblast grafts transplanted into the rat abdominal aorta.

Two animal models, the rabbit and the rat, were used to determine the potential usefulness of the myofibroblast tube as a vascular graft material. Animals suffer no adverse effects from induction and harvesting of multiple peritoneal cavity-derived capsules over several months. The rabbit had a segment of its right carotid artery removed and replaced with the myofibroblast tube, while the rat had its abdominal aorta cut but not removed and a myofibroblast tube inserted at the cut ends. FIG. 10 shows different rabbit carotid arteries before and after blood is permitted to flow through the substitute vessel.

a) Transplantation of rat myofibroblast tube to the rat aorta

Thirty male Wistar rats (250 to 350 g), each containing a 2 week old myofibroblast tube in the peritoneal cavity, were divided into five groups (n=6). The rats were premedicated with atropine (0.25 mg/kg body weight administered intraperitoneally), and anaesthetized with 30 1% v/v ($O_2$) halothane. Under sterile conditions, each animal was prepared for operation by shaving the abdomen, and wiping off excess hair with cotton gauze soaked in an antiseptic solution (Betadine). The myofibroblast tube was harvested from the peritoneal cavity of the same animal into whose abdominal aorta it was to be grafted. Only free-floating capsules were used. The abdominal aorta was exposed by a midline abdominal incision and dissected free from the adjacent vena cava and surrounding tissue.

With the aid of an operating microscope, two vascular clamps were placed on the area above and below the transplant site. The abdominal aorta was resected and elastic recoil of the arteries left a gap of 0.5–1 cm between the cut ends. The silastic tubing was removed from the myofibroblast tube and the graft everted, trimmed and aligned with this gap ready for suturing. Two stay sutures (9-0 silk) were placed at each anastomosis to orient the graft and the artery, and to facilitate the placing of other sutures. The mid-anastomotic site was sutured with 10-0 (22 $\mu$m) Ethilon suture material and round and non-traumatic needles. Suturing at the distal anastomosis was done first, followed by the proximal anastomosis. A total of eight interrupted sutures were placed at each end: one each at the dorsal, ventral, medial and lateral aspect of the anastomosis. Four more sutures were then placed to fill the intervals between them. Interrupted sutures, Ethilon 9-0 (Ethicon, Inc., Thomwood, N.J.) were used. If more sutures were made a tightening effect was seen at the anastomotic sites where there is potential for an anastomotic aneurysm. The use of stay sutures was important, since they prevent accidental suturing of the front and back wall of the same vessel. The grafts were not preclotted, nor was heparin or spasmolytics administered.

When suturing was completed, the distal clamp was released to allow the graft to fill with blood under low pressure, and then the proximal clamp released to allow blood flow under full arterial pressure through the graft. Light external pressure with Gelpro sealant was required at the anastomoses to control initial leakage. Haemostasis was achieved by about 2–3 minutes after removal of the clamps, but the graft was continuously monitored for 10–14 minutes in case of secondary bleeding. Patency was determined by direct inspection. The intestines were then placed back and the wound irrigated with saline solution and closed with Dexon 4-0 sutures. The rats had free access to standard food and water. A graft was deemed successful at the time of operation if it had a fully dilated and pulsing appearance, and a femoral pulse was present. Unsuccessful grafts were usually limp and flaccid, with no detectable pulse.

Six rats from each group were sacrificed at the end of their experimental period (1, 1.5, 2, 3 & 4 months post-implant). At the time of sacrifice, the rats were anaesthetised with Ketamin and Xylazine (1 ml/kg body weight administered intraperitoneally). Patency was evaluated in all transplants taken at 1, 1.5, 2, 3 and 4 months and tissue at 1.5 months was taken for organ bath studies. Remaining tissue was fixed for histological studies (see Example 6). Wall thickness was measured and cell density calculated with the Mocha (Jandel scientific) image analysis using the modified method of Kleinert et al (1996). This was done in all vessels post-transplantation and in trimmed segments of vessels pre-transplantation.

After 1 month and 1.5 months transplantation, grafts in all 6 rats of Group 1 had a pulse and were patent. At 2 months, 4 out of 6 grafts were patent, and at 3 and 4 months there were 3 out of 6 patent grafts, giving an overall patency rate of 73% (Table 2). None of the grafts had been preclotted nor was heparin or spasmolytics administered to the animals at the time of transplantation as the anti-thrombotic benefits of the mesothelial lining were being tested. Non-patent grafts had their lumen blocked by incorporated thrombus and by $\alpha$-smooth muscle actin staining cells. Signs of recanalization were sometimes seen. The patent rat grafts possessed a normal, intact wall and a strong pulse. Mesothelium (or migrated endothelium) which stained for von Willebrand factor comprised the inner lining. The average wall thickness of the graft increased from 0.18±0.02 mm (pre-transplant) to 0.25±0.02 mm by 1 month after which no further change was observed. No significant ($p<0.1$) increase in cell number was evident in the "media", with the increase in graft thickness due to the large amount of extracellular matrix, mainly collagen, which developed on the outer surface of the wall. This "adventitia" contained vasa vasora as seen with antibodies to α-smooth muscle actin.

Figure 14A:
Figure 14B:
Figure 14C:
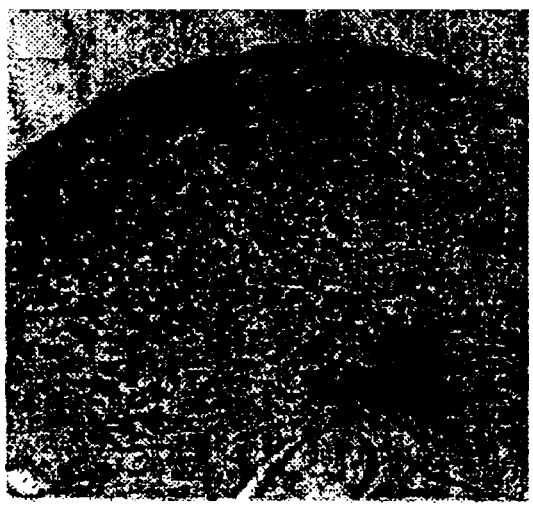
Figure 14D:
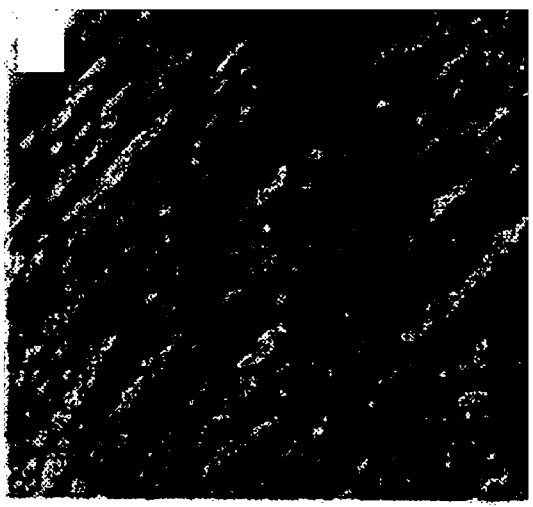

The cells within the wall of the grafts in the rat stained intensely for α-smooth muscle actin and smooth muscle myosin. By 3 months the Vvmyo of the cells in the rat transplant had increased to 58.7±1.4% which was not significantly different from smooth muscle cells in the rat aorta near to the transplant site (Table 4). Structures that resembled elastic lamellae and stained with both Hart's and Weigert's elastic stain began to appear in the grafts by 1 month, at first only near the lumen then throughout the "media" (FIG. 14d).

b) Transplantation of rabbit myofibroblast tube to the rabbit carotid artery

Twenty male New Zealand White cross rabbits (aged 3–4 months), each containing 2 week myofibroblast tubes in their peritoneal cavity, were pre-anaesthetized with 1 ml of SAFFAN (i.v., Gloxovet, Victona, Australia) injected into their marginal ear vein. Continuous anaesthesia was achieved with 2.5% v/v ($O_2$) halothane. The myofibroblast tube was harvested from the peritoneal cavity first. To expose the right carotid artery, a midline incision (approximately in line with the trachea) was made. The surrounding connective tissue was blunt dissected and the submandibular glands clamped and retracted to one side to clear the underlying blood vessels. At all times the operated area was kept moist with saline. The transplanting procedure was similar to that in the rat, however, a longer myofibroblast tube was utilised in the rabbit (20 mm) compared to the rat (10 mm). A 1 cm segment of the carotid artery was resected and elastic recoil of the arteries left a gap of about 2 cin. between the cut ends. The trimmed, everted graft myofibroblast tube (with silastic tubing discarded) was sown into place.

At termination, the animals were anaesthetised and the carotid artery exposed and cleaned from the surrounding tissue. The patency of the transplants was assessed as 70% (Table 2). The animals were perfused through the left ventricle with 2.5% v/v glutaraldehyde. Grafts were removed and post-fixed in glutaraldehyde overnight before being placed inside the tissue processor for wax embedding. A similar histological appearance was seen in rabbit as described above in rat even though different lengths and diameter of grafts were transplanted into different arteries (abdominal aorta and carotid artery, respectively). The myofibroblasts in the wall of the artificial artery differentiated further towards the phenotype expressed by vascular smooth muscle cells, with Vvmyo of about 60%. These cells expressed both α-smooth muscle actin (FIG. 14b) and smooth muscle myosin heavy chain (FIG. 14c). As with the rat transplants, elastin fibres developed one month post-transplantation.

These findings show that an artificial artery grown within the patients own peritoneal cavity (or any other cavity lined by mesothelium) may be used as an autologous arterial transplant into a high pressure site. The myofibroblast graft possesses a living, anticoagulant surface (mesothelial lining) and a living, contractile wall (myofibroblasts/smooth muscle), with tensile strength provided by collagen Type I.

This new type of graft material may open new perspectives in the field of arterial reconstructive surgery. A biosynthetic graft that is grown inside a patient's own body ensures no tissue rejection and limited graft complication. It obviates the need for removing mammary artery or saphenous vein (which are often varicose in the elderly) from the patient, and allows the required diameter and length of graft possibly branched as well as straight) to be grown as a form of "designer artery". Since several grafts can be grown at the same time, it allows for multiple bypass grafting with grafts of different diameter.

EXAMPLE 6

The Myofibroblast Tube Forms a Living, Contractile Conduit

To determine whether the myofibroblast tube functionally behaves in the same manner as the host artery into which it has been transplanted in response to contractile and relaxing agents, the following experiments were carried out.

Figure 12B:
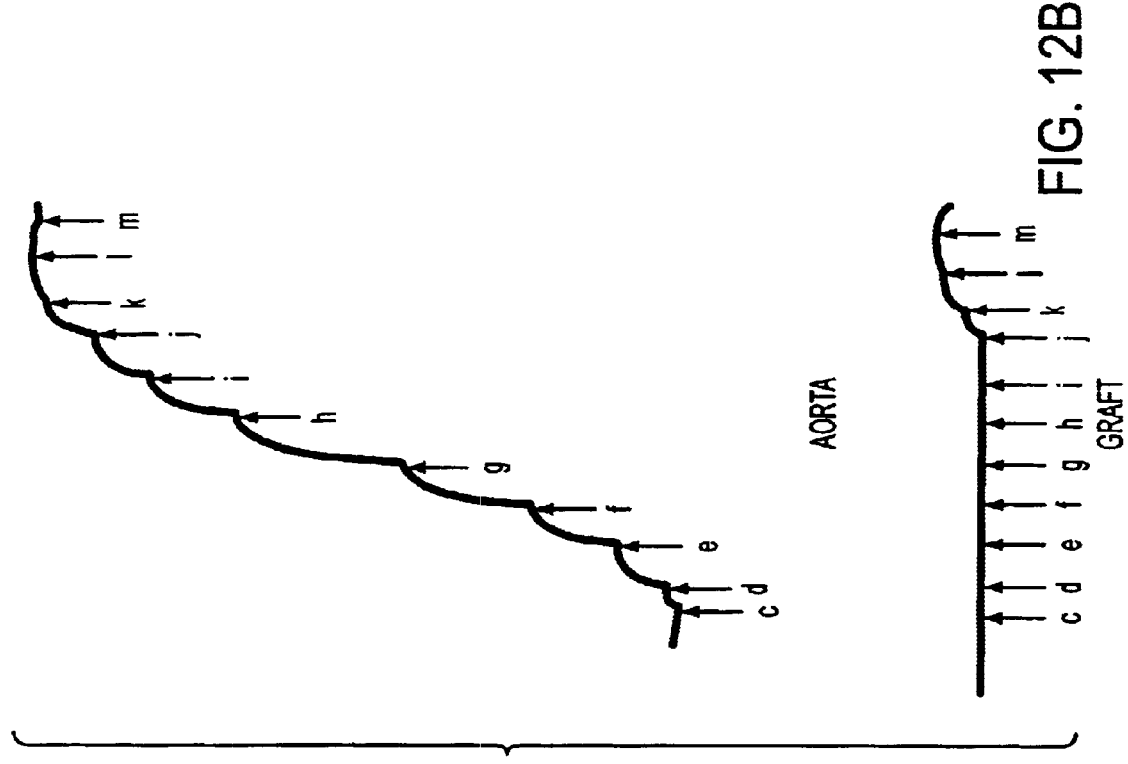
FIG. 12B is a graphical representation showing response of rat thoracic aorta (upper trace) and transplanted graft (lower trace) to phenylephrine at $10^{-9}$ M(c) to $10^{-4}$ M(m)
Figure 12A:
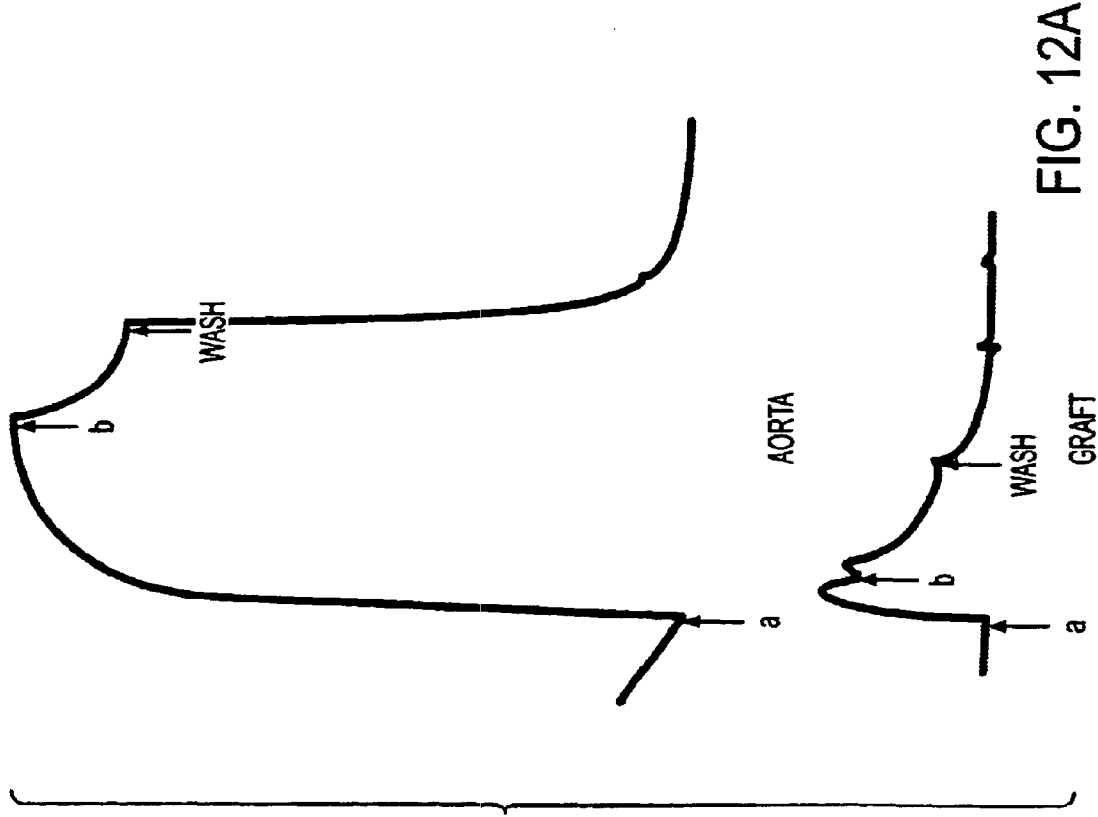
FIG. 12A is a graphical representation showing response of rat thoracic aorta (upper trace) and transplanted graft (lower trace) to 100 mM KCl (a) and $1 \times 10^{-5}$ M acetylcholine (b).

Myofibroblast tubes, grown in the peritoneal cavity of a rat for 2 weeks, were harvested and transplanted into the abdominal aorta of the host as described in Example 5 (a). One and a half months after transplantation, 3 rings from each graft and thoracic aorta from the same animal were suspended on stainless steel wire hooks in a jacketed water bath. After equilibrium conditions were achieved, 100 mM potassium chloride (KCl) was added to the organ bath to determine whether the transplanted graft had any contractile activity. The normal thoracic aorta had an increase in contraction of 16.0 mN while the transplanted graft contracted to 3.8 mN (FIG. 12A). While the rings were contracted, acetylcholine at $10^{-5}$ M was added and both rings relaxed.

Both tissues were then exposed to the contractile agonist 5-hydroxytryptamine (5-HT) from $10^{-9}$ to $3\times10^{-5}$ M. While the thoracic aorta began contracting at $3\times10^{-7}$ M and reached a peak of 19 mN at $3\times10^{-5}$ M, the transplanted graft had no contractile response.

Similar studies were carried out with phenylephrine at $10^9$ to $10^{-4}$ M. The thoracic aorta began contracting at $3\times10^{-9}$ to a maximun of 15.5 mN at $3\times10^{-5}$ M, while the graft contracted at $10^{-6}$ M to reach a maximum of 1.5 mN at $10^{-5}$ M (FIG. 12B).

When the myofibroblast tube was taken directly from the peritoneal cavity after 2 weeks development and tested as above, there was no response to any agonist.

These studies demonstrate that the myofibroblast tube, several weeks after transplantation into the host aorta, begins to acquire the same response to contracting and relaxing agents as the bone fide artery. This has important clinical implications since it demonstrates that the graft is capable of responding to the same circulating regulators of vessel wall tone as the host artery.

EXAMPLE 7

Improvements in Generation of the Myofibroblast Tube in the Rabbit

The following improvements in the generation of the myofibroblast tube have been made in the rabbit model:

Increase in length of myofibroblast tube

In 6 rabbits it was found that lengths of silastic tubing of 60–80 mm and 1.9 mm outer diameter could be used to form a myofibroblast capsule (FIG. 13A). These capsules were complete and of even thickness and when everted formed a tube of living tissue of the same diameter as the common carotid artery into which a 20 mm segment was sutured (FIG. 15B).

Another advantage of tubing of this longer length was that it formed fewer adhesions to the peritoneal fat or the bowel. This may be due to the inability of the longer lengths (rather than 20 mm as previously in the rabbit) to move deep into the peritoneal cavity amongst the intestines.

Addition of 1.5% w/v dextrose in balanced salt solution to the peritoneal cavity A reduction in the rate of adhesion formation (ie fewer adhesions) was achieved, in part, by the addition of 1.5% w/v dextrose in 10–15 ml balanced salt solution added to the peritoneal cavity at the time of tube insertion.

Sterility

In the rat it had been found that thicker capsules of granulation tissue developed if the tubing was unsterile. However, in the rabbit it was shown that capsules of comparable thickness developed when the tubing had been sterilzed in 70% v/v ethanol and air-dried prior to implantation in the peritoneal cavity.

GM-CSF in peritoneal fluid

The addition of 0.02 $\mu$g granulocyte-macrophage colony stimulating factor (GM-CSF) in 10 ml 1.5% w/v dextrose in phosphate buffered saline added at the same time as tube implantation in the peritoneal cavity of the rabbit resulted the development of a very uniform and thick capsule of granulation tissue. This was assumed to result either from an increased number of peritoneal macrophages recruited into the cavity or from proliferation of existing peritoneal macrophages.

Spiral grooves in the silastic tubing

The spiral orientation of smooth muscle cells in blood vessels provides for larger and better control of compliance compared with a structure where the cells and collagen fibres have formed a circumferential or longitudinal array.

Under normal conditions the cells in the granulation tissue that forms on silastic tubing in the peritoneal cavity is in a longitudinal orientation. In order to encourage the myofibroblasts to develop in spiral arrangement around the silastic tubing, rather than a longitudinal orientation, spiral grooves were etched into the tubing with glass paper. This orientation of the myofibroblasts closely resembled the organization of smooth muscle cells in blood vessels.

Coating of tubing

To determine whether coating the silastic tubing resulted in a thicker, even capsule the following substances were applied prior to implantation of the tubing in the peritoneal cavity:

a) Tubing was coated with plasma proteins by incubating sterile tubing in 100% foetal calf serum for 12 hours at 37° C., then thoroughly draining the tubing.

b) Tubing was coated with collagen Type I prepared from rat tail tendons by dipping and drying 3 times.

c) Tubing was coated with fibronectin.

d) Tubing was coated with laminin.

EXAMPLE 8

Improvement in Graft Patency

In Example 5, no anticoagulants or antiplatelet agents or spasmolytics were given to the animals at the time of transplantation, before or later, in order to test the thromboresistance of the mesothelial lining of the implant. Under these conditions, the patency rate was 73% in the Tat (30 rats at 1, 1.5, 2, 3, or 4 months post-transplantation) or 70% in the rabbit ( 20 rabbits at 1, 2, 3, or 4 months post transplantation (see Example 5).

In order to determine whether the addition of heparin improved the patency rate in the rabbit, the following procedure was carried out immediately prior to suturing 20 mm lengths of everted granulation tissue into the rabbit carotid artery:

Heparin at 1000 IU/ml was diluted 1:10 in balanced salt solution, then used to flush and fill both cut ends of the carotid artery at the site where the implant was to be grafted. Once the implant had been sutured into place, the sutured regions were sealed with Gelfoam and then the distal artery clamp was slowly removed allowing heparin solution to slowly enter the transplant. The proximal clamp was then slowly released so that heparin solution, then blood pumped from the heart, gradually entered the transplant, pushing the heparin within the cut end through the transplant and in to the rest of the circulation.

After 4 months, 9 out of 10 transplants in the rabbit carotid artery were still patent, giving a patency rate of 90% (see Table 3) as opposed to 70% for rabbit transplants in the absence of heparin.

EXAMPLE 9

To Determine Whether the "Artificial Artery" is Prone or Resistant to Aneurysmal Degeneration (Bursting), Intimal Hyperplasia and Atherosclerosis The bursting strength of rabbit granulation tissue grafts, both pre- and 3, 6, 9 and 12 months post-transplantation, is determined by applying increased intraluminal pressure via a cannula inserted at one end and a mechanical pressure gauge applied to the cannulated distal end. Also, radial and uniaxial tensile loading in a FastTrack 8800™ Servohydraulic Test System determines tangent Young's modulus (stiffness), yield point, ultimate strength/stress, strain to failure and tissue hysteresis. These values are compared to those of natural carotid artery. The area around ruptures is examined histologically and the thickness of the wall in that region, plus distal sites, measured using image analysis techniques (Mocha, Jandel Scientific). Intimal thickening, if any, at these sites (as a percent of total wall thickness) is determined and all data analysed by one-way ANOVA and the Turkey-Kramer multiple comparison test.

In a separate group of rabbits (n=8), "artificial arteries" are grafted into the right carotid artery. An excised, then sutured back into place, 20 mm segment of left carotid artery acts as an internal control for each rabbit, as manipulation will influence the degree of lipid accumulation. The animals are fed a 1% w/v cholesterol diet for 6 weeks, then the % surface area of the implant covered with lipid-filled (Oil-Red-O staining) lesions determined by image analysis. The values are analysed by paired t-test. The plasma cholesterol levels of all rabbits is measured prior to the commencement of the diet and at termination.

The "artificial blood vessel" as an arteriovenous access fistula (for haemodialysis) The inventors graft a length of autologous "artificial blood vessel" as a femoro-femoral or brachial-cephalic arteriovenous fistula in the rabbit (n=8). The effect of serial (one per week) catheterizations on the patency and morphology of the fistula is determined at 3 months. Currently, haemodialysis patients have a similar procedure done with saphenous vein or ePTFE, however regular catheterization leads to severe damage. and graft failure. "Artificial vessels" are replaced by fresh tubes of non-thrombogenic tissue grown within the patient whenever necessary. Animals suffer no adverse effects from induction and harvesting of multiple peritoneal cavity-derived capsules over several months.

Use of Tenckhoff catheter as a peritoneal dialysis catheter

Improved ways to implant and access the molding are tested using access devices designed for human peritoneal dialysis. Sterile silastic Tenckhoff catheters (Quinton® Instrument Co, USA) with a single or double cuff of Dacron to prevent migration of bacteria and hence peritonitis, and used with or without silicon discs to hold the omentum and bowel away from the tubing. Cut-down versions of these catheters are inserted into the rabbit peritoneal cavity over a guidewire through a small incision, having first infused 15 ml of 1.5% w/v dextrose dialysis solution (plus or minus cytolines/chemokines to increase the number of peritoneal macrophages present). The cuff is sewn in place in the peritoneum, and a Beta-Cap® adapter attached to the external portion of the catheter. This allows peritoneal drainage or the continued addition of fluid. The catheter is surgically removed after 2 weeks, taking care not to damage the granulation tissue capsule. This procedure allows more precise and consistent positioning of the "artificial blood vessel" mold and alleviates invasive harvesting prior to autologous transplantation.

"Artificial blood vessel" can be genetically engineered to improve efficacy Granulation tissue capsules are grown in the rabbit peritoneal cavity. Prior to removing the tubing and everting the tissue, the outer lining of mesothelial cells is transfected for 15 minutes in vitro with an adenoviral construct expressing tissue plasminogen activator or β-galactosidase, with a nonviral buffer) control group (n=8/group). All transfected "vessels" are grafted into the right carotid artery and their patency and histological appearance determined after 6 months. Transfection of vein grafts for plasminogen activator has recently been shown to significantly reduce thrombus formation both within the engineered vein graft and downstream artery (Kuo et al, 1998).

To determine whether the "artificial blood vessel" can be grown in vitro

A vessel is created in vitro with no artificial supporting scaffold but with a scaffold of matrix it has created itself, as with the mesothelial-lined granulation tissue tube formed in the peritoneal cavity of the host. An "artificial blood vessel" formed entirely in vitro avoids the inconvenience to patients of having tubing inserted into peritoneal cavity for 2 weeks.

Living cells are harvested from the rabbit peritoneal cavity through an indwelling Tenckhoff catheter. Macrophage and mesothelial cell numbers are maximised by flushing the peritoneal cavity with cytokines/chemokines and gentle agitation of the wall. Known numbers of harvested cells are resuspended in 1:1 RPMI culture medium and rabbit peritoneal fluid then seeded onto tubes of precoated silastic or other polymer lining the bottom of a culture dish. The tubing is gently rotated after 4 hours to encourage even cell coverage. The development of a tube of tissue is followed histologically over the next few weeks. The everted tissue is grafted into an artery of the small animal from which the cells were harvested.

EXAMPLE 10

Pig Model

Before the tissue tube described herein can be grown and transplanted into humans it is tested in a large animal model.

The pig is of a similar size to humans and has a very similar cardiovascular system, specifically the size and structure of the heart and arteries. Forty pigs (50–1000 Kg) are anaesthetised with intramuscular injection with Ketamine (15 mg/Kg)/Xylazine (1 mg/Kg) then halothane (1–2% v/v) in oxygen via a mask. A sterile silastic Tenckhoff catheter (420 mm long) of outer diameter 5 mm (Quinton® Instrument Co, USA) with a single or double cuff of Dacron to prevent migration of bacteria and hence peritonitis, is inserted into the peritoneal cavity over a guidewire through a small incision, having first infused 100 ml of 1.5% w/v dextrose dialysis solution (plus or minus cytokines/chemokines to increase the number of peritoneal macrophages present). The cuff is sewn in place in the peritoneum, and a Beta-Cap® adapter attached to the external portion of the catheter. This allows the continued addition of fluid, if needed.

The catheter is surgically removed after 2 weeks taking care not to damage the granulation tissue capsule. The tissue capsule is everted and lengths of tissue tube used as bypass grafts in the anterior descending and circumflex coronary arteries, or the carotid, iliac or femoral arties. Patency, bursting strength, elasticity, reactivity to contractile and relaxing agents, and histology of the grafts are tested both pre-transplantation and 1–3 years post-transplantation.

EXAMPLE 11

Eversion of Tissue Tube and Storage Prior to Transplantation

Once the tissue tube is harvested from the peritoneal cavity, it is placed into a sterile petri dish with a scintered glass plate containing cold Hanks' Balanced Salt Solution. The scintered glass plate acts to prevent the tissue tube slipping during the eversion manipulations.

There are two methods to evert the tissue tube:

1. For lengths 40 mm and less.

Requirements:

1× No. 4 watchmaker forceps (sterile) whose arms have been ground thin; 1× normal No. 4 watchmaker forceps (sterile).

Method

Cut both ends of the tissue capsule.

Pass the arms of the ground thin watchmaker forceps through the lumen of the tube and gently grasp the distal cut end in one place.

Gently pull watchmaker forceps back through the lumen, at the same time everting the tissue with aid of the second pair of forceps.

2. For any length of tissue tube.

Requirements:

Sterile tubing or filament of the same outer diameter as the tubing mold;

2× No 4 watchmaker forceps (sterile).

Method

Cut distal end of tissue capsule.

Abutt a piece of sterile tubing to the uncut proximal end of tissue tube plus mold.

With one pair of forceps, gently evert by pushing against cut end of the capsule with a second piece of silastic tubing of the same diameter at the same time threading the tissue over the second piece of tubing. Both pieces of tubing are then discarded.

The everted tissue tube can then be trimmed to the desired length and stored in cold Hanks' Balanced Salt Solution, just covering the tissue to allow maximum oxygenation, for up to 6 hours prior to transplantation.

EXAMPLE 14

Preferred Method for Producing Artificial Vessels in Rabbits

The following methods and steps are employed:

1. Silastic tubing of 1.9 mm outer diameter is cut into 60 mm lengths, then spiral grooves etched into the tubing with glass paper.
2. The tubing is sterilized by soaking in 70% v/v ethanol for 4 hours, rinsed in 100% v/v ethanol then drained and air-dried in a laminar flow cabinet.
3. The tubing is then incubated overnight at 37° C. in fibronectin to enhance attachment of peritoneal macrophages.
4. The animal is anaesthetised with 1.5 ml Dipravan (Propofol, 10 mg/ml, ICI Pharmaceuticals, Vic) and maintained on halothane (ICI Pharmaceuticals, Vic).
5. The abdomen is shaved and surface sterilised with Chorohexidine (0.5% v/v in 70% v/v alcohol) then two pieces of the sterile tubing inserted via a small incision into the peritoneal cavity, at the same time adding 10 ml Hanks' Balanced Salt Solution containing 1.5% w/v dextrose (to help prevent adhesions) and 0.02 $\mu$g GM-CSF (to stimulate macrophage recruitment and proliferation).
6. The peritoneum is sutured and the animal allowed to recover.
7. After 2 weeks the animal is anaesthetised again and the tubing is harvested and placed in cold Hanks' Balanced Salt Solution on a scintered glass plate in a sterile petri dish.
8. The best of the two (or both, if multiple grafts are required) capsules of granulation tissue is everted by pushing against a cut end of the capsule with a second piece of silastic tubing of the same diameter at the same time threading the tissue over the second piece of tubing. Both pieces of tubing are then discarded.
9. The tissue is stored in shallow, cold Hanks' Balanced Salt Solution while the carotid artery is exposed and a 10 mm segment removed.
10. Both of the cut ends of the carotid artery are flushed and filled with 1000 IU/ml heparin diluted 1:10 in Hanks' Balanced Salt Solution.
11. The tissue tube is trimmed to the desired length then sutured by end to end anastomoses with 10-0 DERMALON suture (Sherwood, Davis and Geck Co, USA) between the cut ends of artery.
12. The suture points have GELFOAM (The Upjohn Co, USA) wrapped around them to minimise leakage.
13. The upstream artery clamp is then gently released with some heparin flowing into the graft.
14. The downstream clamp is then gently released so that heparin and then blood slowly enters the graft, at the same time applying gentle pressure to suture areas with Weckcel sponge (Edward Weck Inc, USA).
15. The incision is sutured with 30 DEXONII (Davis and Geck, NSW), and the antbiotic TERRAMYCIN (0.3 in. of 100 mg/ml) (Pfizer, NSW) injected into the thigh muscle.
16. The animal's nails are trimmed and taped to prevent scratching of sutures and the abdomen bandaged with Primapore.
17. The animal is then allowed to recover.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

Comparison of proteins in rat granulation tissue tube, formed in the peritoneal cavity over 2 weeks, with rat aorta using densitometric analysis of Western blots

| Antibodies | Myofibroblast tube protein relative to aorta (% value ± SD, n = 3) |
| --- | --- |
| α-smooth muscle actin | 108 ± 2 |
| β-actin | 560 ± 188 |
| Smooth muscle myosin heavy chain | 23 ± 1 |
| Vimentin | 86 ± 8 |
| Collagen Type I | 76 ± 3 |
| Collagen Type IV | 93 ± 1 |
| Elastin | 9 ± 1 |

TABLE 2

Patency of grafts without heparin with time after transplantation of the rat abdominal aorta or rabbit carotid artery

|  | 1 month | 1.5 months | 2 months | 3 months | 4 months | % patent |
| --- | --- | --- | --- | --- | --- | --- |
| Rat (n = 30) | 6/6 | 6/6 | 4/6 | 3/6 | 3/6 | 73% |
| Rabbit (n = 20) | 4/5 | N/A | 3/5 | 4/5 | 3/5 | 70% |

TABLE 3

Patency of rabbit grafts WITH heparin 4 months after transplantation to the carotid artery

|  | 4 months | % patent |
| --- | --- | --- |
| Rabbit (n = 10) | 9/10 | 90% |

TABLE 4

Volume fraction of myofilaments of spindle shaped cells in 2 week implant harvested from the peritoneal cavity of the rat and after 3 months transplantation into the rat abdominal aorta

| Rat tissue | Volume fraction of myofilaments (V, myo) % n = 60 cells |
| --- | --- |
| 2 week peritoneal implant | 35.7 ± 1.6 |
| 3 months post transplantation | 58.7 ± 1.4* |
| Aorta | 63.7 ± 5.7* |

*$p < 0.1$

BIBLIOGRAPHY

1. Campbell et al, *Arteriosclerosis.* 9(5): 63343, 1989.
2. Desmouliere et al, *Journal of hepatology* 22: 61–64, 1995.
3. Edwards and Roberts *Clin. Mater* 9: 211–223, 1992.
4. Hartig et al, *Brain-Res-Brain-Res-Protoc.* 2(1): 35–43, 1997.
5. Kleinert et al, *Cell Transplant* 5(4): 475–482, 1996.
5. Koch et al, *Aust. NZ. J. of Surg.* 67: 637–639, 1997.
6. Kuo et al, *Am. J. Roentgenol.* 171: 553–558, 1998.
7. Manderson and Campbell, *Journal of Pathology* 18: 77–87, 1986.
8. Puchkov et al, *Morfologia* 1996; 110(5): 15–9, 1996.
9. Sappino et al, *Lab Invest* 63: 144–161, 1990.

10. Schwartz et al, *Mayo Clin Proc* 68: 54–62, 1993.
11. Verhagen et al, *British Journal of Haematology* 95: 542–549, 1996.
12. Walden et al, *Arch-Surg.* 115(10): 1166–9, 1980.

What is claimed is:

1. A method for producing a substitute blood vessel, said method comprising inserting into a peritoneal cavity of a recipient a molding comprising a tube for a time and under conditions sufficient for granulation tissue to form with myofibroblasts, removing the molding from the peritoneal cavity, separating the molding away from the granulation tissue and everting said granulation tissue.

* * * * *

UNITED STATES PATENT AND TRADEMARK OFFICE
CERTIFICATE OF CORRECTION

PATENT NO. : 6,626,823 B1
DATED : September 30, 2003
INVENTOR(S) : Julie Hazel Campbell et al.

It is certified that error appears in the above-identified patent and that said Letters Patent is hereby corrected as shown below:

Title page,
Item [73], Assignee, change "The University of Queenland of St. Lucia" to
-- The University of Queensland --.

Signed and Sealed this

Eighth Day of March, 2005

JON W. DUDAS
*Director of the United States Patent and Trademark Office*